(12) United States Patent
Kuwahara et al.

(10) Patent No.: US 6,211,404 B1
(45) Date of Patent: Apr. 3, 2001

(54) METHOD OF REFINING BENZOIC ACID

(75) Inventors: Hiroyuki Kuwahara; Yuji Arifuku; Kazuyoshi Horibe, all of Kitakyushu; Nobumasa Noma, Fukuoka-ken; Masakazu Takeuchi, Yukuhashi; Haruki Kawano, Tokai, all of (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/269,552

(22) PCT Filed: Sep. 29, 1997

(86) PCT No.: PCT/JP97/03472

§ 371 Date: Mar. 30, 1999

§ 102(e) Date: Mar. 30, 1999

(87) PCT Pub. No.: WO98/14420

PCT Pub. Date: Apr. 9, 1998

(30) Foreign Application Priority Data

Sep. 30, 1996 (JP) .................................................. 8-258722

(51) Int. Cl.$^7$ ................................................ C07C 51/42
(52) U.S. Cl. ........................ 562/494; 422/245.1; 422/261
(58) Field of Search ........................ 562/494; 422/245.1, 422/261

(56) References Cited

U.S. PATENT DOCUMENTS

| | | | |
|---|---|---|---|
| 3,410,923 | * 11/1968 | Strand et al. | ........................ 585/816 |
| 4,004,886 | * 1/1977 | Thijssen et al. | ................... 422/245.1 |
| 4,547,587 | * 10/1985 | Kleintjens et al. | ................... 562/494 |
| 4,588,414 | * 5/1986 | Takegami et al. | ................... 23/295 R |
| 4,652,675 | * 3/1987 | Goorden et al. | ...................... 562/494 |
| 5,466,266 | * 11/1995 | Griffiths | .............................. 23/295 R |
| 5,755,975 | * 5/1998 | Eck et al. | .............................. 210/714 |

FOREIGN PATENT DOCUMENTS

| | | |
|---|---|---|
| 54-141745 | 11/1979 | (JP) . |
| 56-152702 | 11/1981 | (JP) . |
| 57-99301 | 6/1982 | (JP) . |
| 59-66305 | 4/1984 | (JP) . |
| 61-130257 | 6/1986 | (JP) . |
| 61-25013 | 6/1986 | (JP) . |
| 6-91103 | 4/1994 | (JP) . |
| 6-43367 | 6/1994 | (JP) . |

OTHER PUBLICATIONS

Synopsis of Lecture at the Technology Committee, "Present State of the Crystallization Purification Processes," 9$^{th}$ Symposium on the Industrial Crystallization, Jan. 1985.

* cited by examiner

*Primary Examiner*—Gary Geist
*Assistant Examiner*—Taylor V. Oh
(74) *Attorney, Agent, or Firm*—Birch, Stewart, Kolasch & Birch, LLP

(57) ABSTRACT

This invention relates to a process for purifying benzoic acid continuously to a purity of 99.9% or more by introducing crystals of crude benzoic acid with a bulk density of 0.2 g/cm$^3$ or more and an average particle diameter of 0.3 mm or more into a continuous crystallization apparatus equipped with a stirrer and a heating device from the upper portion of the apparatus, effecting counter-current contact of the falling crystals of crude benzoic acid with the melt generated by heating with the heating device, withdrawing the purified benzoic acid as melt from the lower portion of the apparatus, and withdrawing the mother liquor from the upper portion of the apparatus. The process makes it possible to prepare high-purity benzoic acid continuously in a relatively simple apparatus at high efficiency.

8 Claims, 1 Drawing Sheet

METHOD OF REFINING BENZOIC ACID

This application is the national phase under 35 U.S.C. §371 of prior PCT International Application No. PCT/JP97/03472 which has an International filing date of Sep. 29, 1997 which designated the United States of America.

FIELD OF TECHNOLOGY

This invention relates to a process for purifying benzoic acid.

BACKGROUND TECHNOLOGY

Benzoic acid can be prepared by a process such as oxidation of toluene. For example, there is a report that the liquid phase oxidation of toluene gives benzoic acid in a yield of 40% or so. Benzoic acid obtained by a process such as mentioned above contains a small amount of impurities even after removal of low-boiling substances such as toluene beforehand. The impurities here include benzaldehyde, benzyl alcohol, benzoic acid esters, biphenyls, p-phenylbenzoic acid, phthalic anhydride and toluic acid and, as they cause problems relating to emission of odor and coloration, they should desirably be removed from the product benzoic acid.

The following processes are known for the purification of benzoic acid: treatment with sulfuric acid followed by rectification as disclosed in Japan Kokoku Tokkyo Koho Sho 61-25013 (1986); vaporization in an inert gas followed by crystallization under specified conditions as disclosed in Japan Kokoku Tokkyo Koho Sho 57-11899 (1982); distillation in the presence of aliphatic amines as disclosed in Japan Kokoku Tokkyo Koho Hei 6-43367 (1994); and purification by supercritical extraction as disclosed in Japan Kokai Tokkyo Koho Sho 61-130257 (1986). None of these processes, however, satisfied all the factors involved in purification such as efficiency, equipment, and cost.

A process based on crystallization such as recrystallization is also known for the purification of crystalline solids, but this too faces the aforementioned problems and is not well suited for application on a commercial scale.

An object of this invention is to provide a process for purifying benzoic acid which permits of continuous preparation of high-purity benzoic acid in a relatively simple equipment at high efficiency.

DISCLOSURE OF THE INVENTION

Accordingly, this invention relates to a process for purifying benzoic acid comprising introducing crystals of crude benzoic acid, 0.2 g/cm$^3$ or more in bulk density and 0.3 mm or more in average particle diameter, into a continuous crystallization apparatus equipped with a stirrer and a heating device from the upper portion of the apparatus, effecting purification by counter-current contact of the crystals of crude benzoic acid falling through the inside of the apparatus with the melt generated by heating with the aforementioned heating device, withdrawing the purified benzoic acid as melt from the lower portion of the apparatus, and withdrawing the mother liquor from the upper portion of the apparatus.

Crude benzoic acid to be purified in this invention is the reaction product of the liquid phase oxidation of toluene from which solids and low-boiling substances such as toluene have been removed, but is not limited to this particular material. Furthermore, the purity of crude benzoic acid is preferably 90% or more, more preferably 95% or more.

Crude benzoic acid is used as crystals with the bulk density controlled at 0.2 g/cm$^3$ or more, preferably 0.3 g/cm$^3$ or more, more preferably 0.4 g/cm$^3$ to 0.8 g/cm$^3$. Crystals of such bulk density can be obtained, for example, by melting, crystallizing, and scraping crude benzoic acid in a flaker drum. In addition, the average particle diameter of crude benzoic acid is 0.3 mm or more, preferably 0.5 mm or more, more preferably 1 mm to 10 mm. As the term of average implies here, powders and coarse particles may naturally coexist. Coarse particles with a particle diameter in excess of 30 mm are desirably removed as much as possible, but those with a particle diameter of 100 mm or so may be kept in without harm as long as the thickness is 1 mm or less. This means that the preferable shape is flake.

The bulk density as used in this invention is determined by placing 100 g of crystals of benzoic acid in a 1000 cc measuring cylinder, shaking for 30 seconds by a vibrator, and reading off the graduation of the measuring cylinder. The average particle diamter is determined by picking out some particles of average size, measuring the length (x), width (y) and height (z), calculating (x+y+z)/3, and averaging the calculated values.

A continuous crystallization apparatus equipped with a stirrer to be used in this invention may be any of vertical tower type crystallization apparatuses provided with an opening for introducing raw material and an opening for withdrawing the mother liquor in the upper portion and a heating device and an opening for withdrawing the product in the lower portion. A variety of apparatuses may be used, but an apparatus such as described in Japan Tokkyo Kokoku Koho Sho 58-46322 (1983) and "Aromatics," Vol. 37 (1985), pages 109–127 or its partially improved version is preferable. Particularly desirable is the aforementioned apparatus from which the cooling device in the upper portion is removed.

Figure 1:
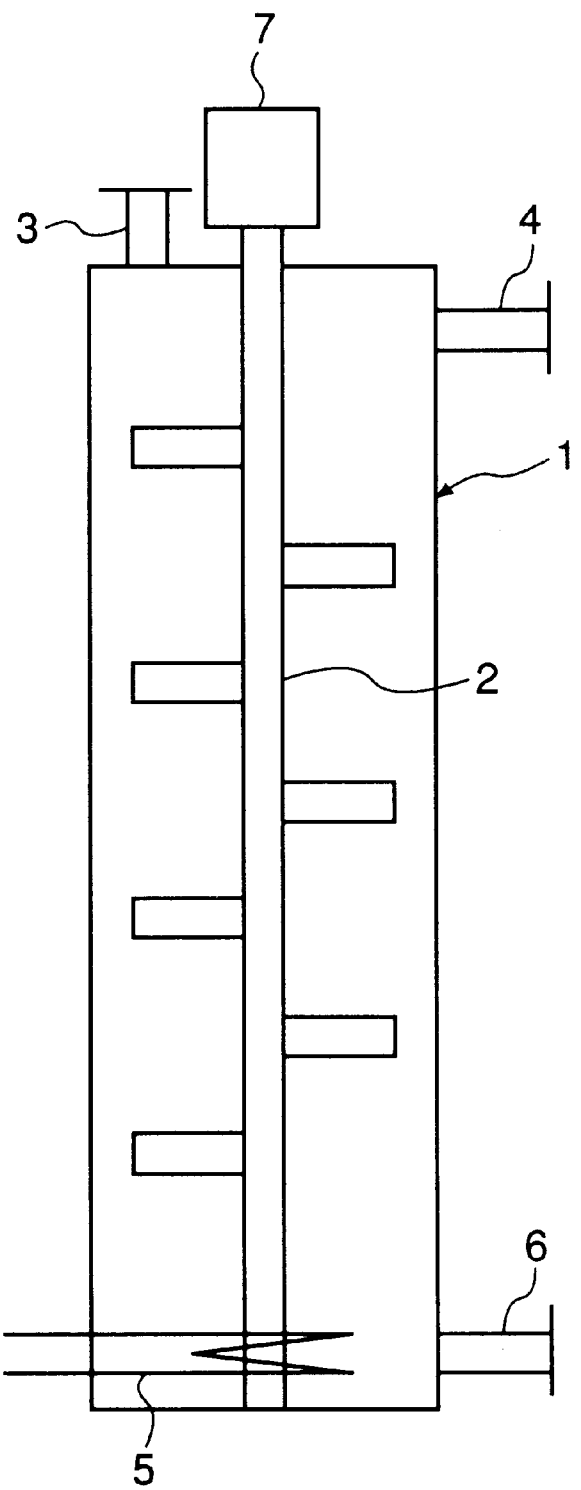
FIG. 1 is a conceptual drawing of one example of a continuous crystallization apparatus. The symbols stand for the following.

1 Main body of apparatus
2 Stirrer
3 Opening for introducing raw material
4 Opening for withdrawing mother liquor
5 Heating device
6 Opening for withdrawing product
7 Driving motor

PREFERRED EMBODIMENTS OF THE INVENTION

This invention will be described with reference to the drawing.

FIG. 1 shows one example of a vertical tower type continuous crystallization apparatus: the main body 1 of the apparatus is equipped with the stirrer 2 inside and is further provided with the opening for introducing raw material 3 and the opening for withdrawing mother liquor 4 in the upper portion and with the heating device 5 and the opening for withdrawing product 6 in the lower portion. The symbol 7 refers to a driving mortor for the stirrer 2.

The stirrer 2 here is desirably a type which performs agitation primarily in the same plane. The type which performs vigorous agitation up and down disturbs the temperature gradient. In the aforementioned preferable type of crystallization apparatus, a layer of the mother liquor is present in the upper section while a layer of slurry consisting of crystals and liquid is present in the middle and lower sections and a temperature gradient develops with the temperature rising from the upper section to the lower section.

Crystals of crude benzoic acid with the specified density and particle diameter as raw material are introduced through the opening for introducing raw material 3. The raw material crystals thus introduced fall slowly and reach the slurry layer with a portion of them melting upon contact with the mother liquor and crystallizing. In the slurry layer, the crystals melt upon contact with the reflux stream and undergo purification by recrystallization, and the crystals whose purity has been raised precipitate while the impurities move into the reflux stream, that is, the mother liquor. The purified crystals are melted by the heating device 5 provided in the lower portion of the main body 1, a portion is withdrawn as product from the opening for withdrawing product 6 and another portion rises as reflux stream.

In this invention, crystals of crude benzoic acid with the specified density and particle diameter are introduced as raw material. Where the raw material is introduced as liquid or as solid not satisfying the specified density and particle diameter, the layer of mother liquor becomes difficult to distinguish clearly from the slurry layer, the temperature gradient does not develop to a specified condition, and a stable operation of the apparatus becomes impossible. This seems to be the main reason why no attempt has been made to purify benzoic acid by crystallization. It is even possible here to introduce the raw material as slurry if it has the specified density and particle diameter.

The operating conditions of the crystallization apparatus vary as well with the purity of raw material, shape and size of apparatus, and the like, and it is preferable to control the temperature of the main body 1 at approximately 122° C. in the lower section, at 110 to 120° C. in the upper section, and at a point in the intermediate range of the foregoing two in the middle section. To establish a temperature gradient such as this, the main body 1 may be jacketed for heating or cooling, but heat insulation alone is sufficient. Cooling of the periphery of the main body 1, particularly the periphery of the upper section, tends to cause problematical precipitation of fine crystals. As the raw material is introduced in the form of crystals in this invention, the heat of melting of the crystals advantageously serves to cool the mother liquor or reflux stream and induce recrystallization. In consequence, there is no ill effect if the raw material is introduced at room temperature.

In this invention, introduction of crystals of crude benzoic acid with the specified density and particle diameter is likely to produce the following effect: the crystals fall smoothly through the layer of mother liquor and reach the slurry layer and, meanwhile, they cover and hold them down fine crystals generated in the apparatus and make clear the distinction between the layers of slurry and mother liquor. The stirrer acts to promote the contact between crystals and reflux stream and raise the efficiency of purification.

EXAMPLE 1

The crystallization apparatus used was a vertical tower type continuous crystallization apparatus such as shown in FIG. 1 consisting of the main body 1, 50 mm in diameter (diameter of tower) and 600 mm in height (height of tower), and the stirrer 2 composed of a stirring axis and bar-shaped stirring blades attached to the axis at intervals of 50 mm.

Crystals of crude benzoic acid to be used as raw material are flakes with a bulk density of 0.45 g/cm$^3$, thickness of 0.45 mm, average diameter of 5.0 mm, and purity of 98% prepared by processing crude benzoic acid prepared by the liquid phase oxidation of toluene into flakes in a flaker drum.

The aforementioned crystals of crude benzoic acid were introduced as raw material into the main body 1 at a rate of 400 g/h through the opening for introducing raw material 3 and the apparatus was operated in the steady state while maintaining the height of the layer of mother liquor in the upper section at approximately 150 mm and the height of the slurry layer in the middle and lower sections at approximately 400 mm and the speed of the stirrer 2 at 50 rpm. The temperature was 118° C. in the upper section, 119° C. in the middle section, and 122° C. in the lower section.

The melt of purified benzoic acid as product was withdrawn at a rate of 200 g/h from the opening for withdrawing product 6 and the mother liquor was withdrawn at a rate of 200 g/h from the opening for withdrawing mother liquor 4. The purity of the product was 99.99% and the concentration of benzoic acid in the mother liquor was 96%.

EXAMPLE 2

The procedure for purification was followed as in the aforementioned Example 1 except setting the speed of the stirrer 2 at 100 rpm, introducing the raw material at a rate of 500 g/h through the opening for introducing raw material 3, and withdrawing the melt of purified benzoic acid at a rate of 350 g/h from the opening for withdrawing product 6. The purity of the product thus obtained was 99.97%.

The temperature inside the main body 1 during the purification operation was 116° C. in the upper section, 119° C. in the middle section, and 122° C. in the lower section.

EXAMPLE 3

The procedure for purification was followed as in the aforementioned Example 1 except setting the speed of the stirrer 2 at 100 rpm, introducing the raw material at a rate of 500 g/h through the opening for introducing raw material 3, withdrawing the melt of purified benzoic acid at a rate of 400 g/h from the opening for withdrawing product 6, withdrawing the mother liquor at a rate of 200 g/h from the opening for withdrawing mother liquor 4, and returning one half, or 100 g/h, of the withdrawn mother liquor to the main body 1 through the opening for introducing raw material 3. The purity of the product thus obtained was 99.95%.

The temperature inside the main body 1 during the purification operation was 113° C. in the upper section, 118° C. in the middle section, and 122° C. in the lower section.

EXAMPLE 4

The procedure for purification was followed as in the aforementioned Example 1 except using flakes (bulk density 0.45 g/cm$^3$, thickness 0.3 mm, average diameter 0.7 mm, and purity 98%) as raw material, introducing the raw material at a rate of 300 g/h through the opening for introducing raw material 3, and withdrawing the melt of purified benzoic acid at a rate of 150 g/h from the opening for withdrawing product 6. The purity of the product thus obtained was 99.99%.

INDUSTRIAL APPLICABILITY

The purification process of this invention makes it possible to prepare benzoic acid with a purity of 99.9% or more easily in a relatively simple apparatus at a low operating cost and is extremely effective industrially.

What is claimed is:

1. A process for purifying benzoic acid comprising:
   introducing, into a continuous crystallization apparatus equipped with a stirrer and a heating device, crystals of crude benzoic acid with a bulk density controlled at 0.2 g/cm$^3$ or more and an average particle diameter of 0.3 mm or more, from an upper portion of said apparatus;

effecting purification by counter-current contact of the crystals of crude benzoic acid falling through inside of the apparatus with a melt generated by heating with said heating device;

withdrawing purified benzoic acid as melt from a lower portion of the apparatus; and withdrawing mother liquor from the upper portion of the apparatus.

2. A process for purifying benzoic acid as described in claim 1 wherein said continuous crystallization apparatus is a vertical tower continuous crystallization apparatus containing a layer of mother liquor of approximately 110 to 120° C. in the upper section, a layer of slurry in the intermediate and lower sections, and a layer of melt of approximately 122° C. in the lower section and crystals of crude benzoic acid are introduced into said apparatus in such a manner as to let at least a part of the crude crystals reach the upper portion of the layer of slurry thereby distinguishing clearly the layer of slurry from the layer of mother liquor.

3. A process for purifying benzoic acid comprising:

introducing, into a continuous crystallization apparatus equipped with a stirrer and a heating device, crystals of crude benzoic acid with a bulk density controlled at 0.2 g/cm$^3$ or more and an average particle diameter of 0.3 mm or more, from an upper portion of said apparatus;

effecting purification by counter-current contact of the crystals of crude benzoic acid falling through inside of the apparatus with a melt generated by heating with said heating device, wherein said purification is effected by repeated dissolving and crystallizing of benzoic acid as it falls through said apparatus and wherein a temperature gradient exists in said apparatus from a low temperature at the top of said apparatus to a high temperature at the bottom of said apparatus;

withdrawing purified benzoic acid as melt from a lower portion of the apparatus; and withdrawing mother liquor from the upper portion of the apparatus.

4. A process for purifying benzoic acid as described in claim 3 wherein said continuous crystallization apparatus is a vertical tower continuous crystallization apparatus containing a layer of mother liquor of approximately 110 to 120° C. in the upper section, a layer of slurry in the intermediate and lower sections, and a layer of melt of approximately 122° C. in the lower section and crystals of crude benzoic acid are introduced into said apparatus in such a manner as to let at least a part of the crude crystals reach the upper portion of the layer of slurry thereby distinguishing clearly the layer of slurry from the layer of mother liquor.

5. The process of claim 3, wherein said crude benzoic acid crystals have a bulk density of 0.4 to 0.8 g/cm$^3$ and an average particle diameter of 1 mm to 10 mm.

6. The process of claim 5, wherein said crude benzoic acid has a purity of 90% of more.

7. The process of claim 5, wherein said crude benzoic acid has a purity of 95% or more.

8. The process of claim 3, wherein said process produces benzoic acid with a purity of 99.9% or more.

* * * * *